United States Patent [19]

Otte et al.

[11] 4,423,721
[45] Jan. 3, 1984

[54] DEVICE FOR INSERTION AND EXTRACTION OF MEDULLARY NAILS

[75] Inventors: Wolf-Dieter Otte; Heinz Otte, both of Volkach, Fed. Rep. of Germany; Siegfried Schider, Reutte; Otto Wiesner, Reutte-Muehl, both of Austria

[73] Assignee: Schwarzkopf Development Corporation, New York, N.Y.

[21] Appl. No.: 351,127

[22] PCT Filed: Sep. 4, 1979

[86] PCT No.: PCT/US79/00710

§ 371 Date: May 9, 1980

§ 102(e) Date: May 9, 1980

[87] PCT Pub. No.: WO80/00534

PCT Pub. Date: Apr. 3, 1980

[30] Foreign Application Priority Data

Sep. 4, 1978 [AT] Austria .................................. 6367/78

[51] Int. Cl.³ .............................................. A61F 5/04
[52] U.S. Cl. .............................. 128/92 EC; 128/92 R; 145/30.5
[58] Field of Search ........... 128/92 EC, 92 R, 92 BA, 128/92 BC, 92 EB, 92 ED; 145/21, 29 R, 29 B, 30.5, 61 F

[56] References Cited

U.S. PATENT DOCUMENTS

| 462,252 | 11/1891 | Gillette. | |
|---|---|---|---|
| 1,747,053 | 2/1930 | Colerick | 145/61 F |
| 3,036,482 | 5/1962 | Kenworthy et al. | 128/92 EC |
| 3,208,450 | 9/1965 | Abelson | 128/92 EC |

FOREIGN PATENT DOCUMENTS 1022328  3/1966  United Kingdom ........... 128/92 EC

OTHER PUBLICATIONS

Zimmer Mfg. Co., Catalog published 1953, vol. 35–A, p. 17, see item #460.
Richards Mfg. Co., Catalog published 1974, p. 72, see item 11–1119S.

Primary Examiner—C. Fred Rosenbaum
Assistant Examiner—C. W. Shedd
Attorney, Agent, or Firm—Morgan, Finnegan, Pine, Foley & Lee

[57] ABSTRACT

A metallic device for the insertion and extraction of medullary nails having a guide tube (1) which is comprised of two successive longitudinal sections (2 and 3). Striking elements (7 and 11) are disposed on opposite ends of the tube and a displaceable strike bushing (6) is located on the tube between the striking elements.

4 Claims, 2 Drawing Figures

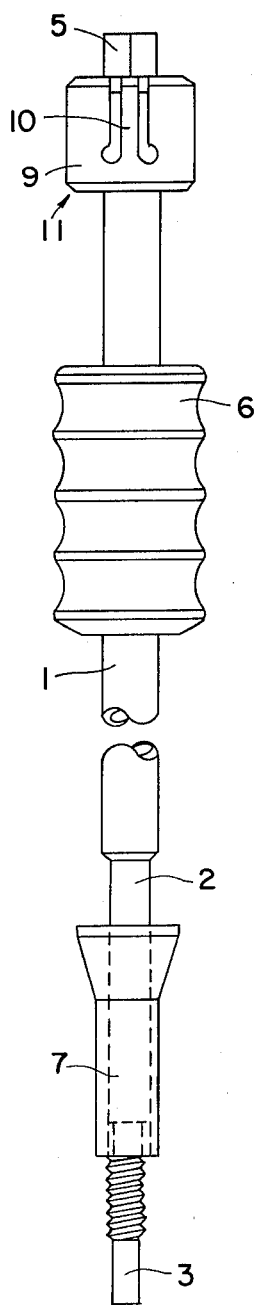
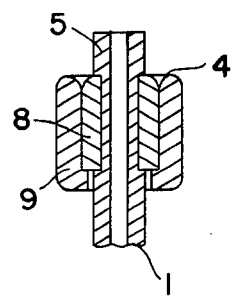

DEVICE FOR INSERTION AND EXTRACTION OF MEDULLARY NAILS

The invention relates to a metallic device for the insertion and extraction of medullary nails the device consisting of a guide tube, striking devices on both ends, and a strike bushing.

It is known practice to drive a medullary nail into the predrilled medullary cavity by means of a striker formed like a chisel and with a hammer. To guide the nail, a guide spit is driven into the medullary cavity as the medullary canal is being bored. For extraction, a nail catcher is used which has a hook on one side that is hooked into a slit type opening in the nail. The end on the other side of the nail catcher is bent and forms an abutment, which is struck by a specially formed hammer which can be moved parallel to the nail catcher.

It is also known in some forms of nails to screw in the nail catcher in a threaded opening in the nails.

These known tools present problems such as optimum transmission of force in the axial direction of the nail and the possibility of injury due to slipping of the hammer or the striker.

From DT-GM No. 75 18 496 and DT-GM S No. 48 682 there are known knock-out devices consisting of a guide rod provided with a knock-out bushing that is displaceable concentrically with respect to the rod and a striking device at the end farthest from the medullary nail. In one embodiment, the guide rod is screwed to the medullary nail. In the other embodiment, it is clamped to the nail by means of a slotted sleeve and a wedge. These devices exhibit disadvantages since their usefulness is for the knocking out of a medullary nail, and as well, they employ an unwieldy strike bushing, since the latter is made of steel and it must be of a very large size to obtain the necessary extraction force.

In contradistinction, it is the object of the present invention to provide a device for the insertion and extraction of medullary nails which consists of a guide tube, striking devices on both ends of the tube, and a strike bushing, which does not have the mentioned disadvantages.

This problem is solved according to the invention by providing a guide tube that is recessed that is provided with two successive longitudinal section, the tube diameters diminishing at the transitions or junctures between the individual longitudinal sections and the portion of the inner longitudinal section towards the medullary nail being threaded. Further the striking device provided on this end is an insertion sleeve which is displaceably disposed on the inner longitudinal tube section being concentrically and slidably disposed thereon and having on the end towards the strike bushing a thickened portion in the form of a truncated cone. Moreover the strike bushing is made of heavy metal or alternatively of heavy metal powder surrounded by a steel jacket and the two striking devices are removable from the guide tube.

The removable striking device at the end of the guide tube farthest from the medullary nail is a three-piece construction. A two-piece sleeve, which has a larger outside diameter than the guide tube, is placed on a longitudinal section of the guide tube which is recessed to a smaller diameter and is held by a clamping sleeve which is fitted on therein.

The outer offset longitudinal section of the guide tube, whose diameter is slightly smaller than the core diameter of the thread of the inner longitudinal section, results in proper guiding when the guide tube is being screwed into the meduallary nail.

A circlip in the interior of the insertion sleeve and a spring tongue provided on the clamping sleeve prevent these parts from falling down when the tool is being handled.

An embodiment of the invention is described below with reference to the figures.

FIG. 1 is an elevational view of the assembled tool;

FIG. 2 is a sectional view through the end of the guide tube farthest from the medullary nail and through the striking device.

Referring to FIG. 1 there is shown there guide tube 1, whose inside diameter is dimensional so that together with the screwed-on medullary nail it can be displaced over the guide spit, be driven into the bone and still partially projecting therefrom. The recessed inner longitudinal section 2, which is contiguous to the recessed outer longitudinal section 3 at the end of the guide tube towards the medullary nail, is somewhat longer than the insertion sleeve 7 and is provided, in a portion near the nail, with a thread for screwing the same into the special medullary nail. The diameter of section 3 is slightly smaller than the core diameter of the thread and thus ensures proper guiding of the guide tube when screwing the same into the medullary nail. An insertion sleeve 7 is displaceably disposed over the inner longitudinal section 2 of the guide tube, being concentrically and slideably disposed thereon. It is prevented from falling down due to its dead weight by means of a circlip. Insertion sleeve 7, which during driving in or insertion of a medullary nail rests on the head of the nail and is struck with the driving force of insertion bushing 6 of which is made of heavy metal or alternatively of heavy metal powder surrounded by a steel jacket. Bushing 6 is displaceably disposed on the guide tube 1, being concentrically and slidably disposed thereon, thus driving the medullary nail into the medullary canal.

Turning next to FIG. 2 there is illustrated there the end of guide tube 1 farthest from the nail. At that portion, the tube is provided with a longitudinal section 4 recessed to a smaller diameter and on which is fitted a two-piece sleeve 8 which has an outside diameter greater than the outside diameter of the guide tube 1. A clamping sleeve 9 provided with a collar directed towards the strike bushing and applying sleeve 8 against the guide tube 1 is slipped over sleeve 8. A spring tongue 10 retains the clamping sleeve 9 in place.

These removable parts serve as an abutment device when knocking out a medullary nail and also prevent the unintentional sliding of the insertion bushing 6 over the end of guide tube 1 during the driving in or insertion of a medullary nail.

The end 5 of guide tube 1 farthest from the nail is hexagonally shaped and a wrench can be applied thereto. Thus rotation of the nail and hence better positioning during insertion and better release of the nail from the medullary canal during extraction is made possible.

In contrast to the disadvantages in known devices for the insertion and extraction of medullary nails, such as for example, an unwieldy large extraction bushing, the possibility of injury on insertion and extraction, and less than optimum transmission of force to the medullary nail, the device of this invention for insertion and extraction of medullary nails presents many advantages such as are enumerated below.

One advantage attainable by the present invention resides in the fact that by the combination of concentric guiding of the strike bushing 6 on the guide tube 1 and production of the strike bushing 6 of heavy metal or of a heavy metal powder surrounded by a steel jacket, optimum transmission of force to the medullary nail both with respect to magnitude and direction is made possible.

Another advantage of the present invention is that due to insertion sleeve 7 being concentrically disposed and slidably displaceable on the inner longitudinal section 2 of the tube and which bushing contacts or is applied against the head of the nail as it is being driven in, the threaded union of the guide tube 1 and the medullary nail is not loaded by the driving force. In addition, any exposed thread is covered, so that jamming or damage to the thread is ruled out. Since both strike devices, 11 and 7, and also the strike bushing 6 are removable, proper cleaning and sterilization of the tool is made possible.

We claim:

1. In a metallic device for insertion and extraction of medullary nails, comprising a guide tube (1) with striking elements (7,9) on both ends thereof, a displaceable strike bushing (6) disposed concentrically and slidably relative to said guide tube, said striking elements being removable from said guide tube, the improvement comprising the end of the guide tube towards the medullary nail has a doubly reduced diameter in two successive longitudinal sections (2,3), said tube diameter diminishing to the diameter of the successive section at each transition between the individual longitudinal sections; the end longitudinal section (3) towards the medullary nail having the smallest diameter and being threaded; the intermediate longitudinal section, between said guide tube and said end section, having concentrically disposed thereabout one of said striking elements, said striking element including an insertion sleeve (7) which is with said striking element slidably displaceable on said intermediate section; during insertion of said nail, said insertion sleeve bears against the end face of said nail and delivers directly thereto the force imported by striking said striking element with said strike bushing; said strike bushing being made from a composition having a density greater then 10 g/cm$^3$ wherein said composition is a material selected from the group consisting of a sintered composite of principally tungsten with metalic binders or a metal powder encased in a steel jacket.

2. A device according to claim 1, wherein the striking element (9) disposed at the end of the guide tube (1) farthest away from the medullary nail comprises a two-piece sleeve (8) of larger outside diameter than that of said guide tube (1), the sleeve (8) being placed on a longitudinal section (4) of the guide tube (1) recessed to a smaller diameter, and a clamping sleeve (9) slipped over said sleeve (8) with a collar directed toward the striking bushing (6).

3. A device according to claim 2, wherein the clamping sleeve (9) is comprised of a spring tongue (10) which exerts pressure on said two-piece sleeve (8) and retains same on said recessed longitudinal section of the guide tube.

4. A device according to claim 1, wherein the end (5) of the guide tube (1) farthest from the medullary nail has a hexagonal form.

* * * * *